United States Patent
Eguchi et al.

(10) Patent No.: US 8,222,614 B2
(45) Date of Patent: Jul. 17, 2012

(54) ELECTRON BEAM IRRADIATION APPARATUS FOR OPEN-MOUTHED CONTAINERS

(75) Inventors: Shiro Eguchi, Chiba (JP); Tomoyuki Hikosaka, Ichihara (JP); Satoru Gohzaki, Ichihara (JP); Takayuki Suzuki, Kisarazu (JP); Shigekatsu Sato, Hitachi (JP); Isao Hashimoto, Hitachi (JP)

(73) Assignee: Japan AE Power Systems Corporation, Tokyo (JP)

( * ) Notice: Subject to any disclaimer, the term of this patent is extended or adjusted under 35 U.S.C. 154(b) by 71 days.

(21) Appl. No.: 12/992,082

(22) PCT Filed: May 12, 2008

(86) PCT No.: PCT/JP2008/059096
§ 371 (c)(1),
(2), (4) Date: Nov. 10, 2010

(87) PCT Pub. No.: WO2009/139074
PCT Pub. Date: Nov. 19, 2009

(65) Prior Publication Data
US 2011/0084221 A1 Apr. 14, 2011

(51) Int. Cl.
*H01J 37/20* (2006.01)
(52) U.S. Cl. .............. 250/455.11; 422/22; 422/186
(58) Field of Classification Search .......... 250/455.11, 250/453.11; 422/22, 24, 186, 292
See application file for complete search history.

(56) References Cited

U.S. PATENT DOCUMENTS 7,767,987 B2 * 8/2010 Eguchi et al. ............. 250/492.3
2009/0110613 A1 * 4/2009 Naka et al. ................. 422/186

FOREIGN PATENT DOCUMENTS

| JP | 10-268100 | 10/1998 |
| JP | 11-001212 | 1/1999 |
| JP | 11-137645 | 5/1999 |
| JP | 2002-104334 | 4/2002 |
| JP | 2007-522833 | 8/2007 |
| WO | 2007/046213 A1 | 4/2007 |

* cited by examiner

*Primary Examiner* — Kiet T Nguyen
(74) *Attorney, Agent, or Firm* — Brundidge & Stanger, P.C.

(57) ABSTRACT

The apparatus has a rotating body 11 in an irradiation processing chamber 10. Outside the rotating body 11, plural retaining mechanisms 2 are installed at regular interval to retain open-mouthed containers. Above the conveying path, an electron beam generating means 40 is arranged. The rotating body 11 has a rotary shaft 12 that penetrates into the electron beam generating means 40. On the rotary shaft 12, a grid plate 45 of an electron beam source 41 of the electron beam generating means 40 is rotatively installed. On the grid plate 45, plural emission holes 46 are provided at the same interval as that of the retaining mechanisms 2 on the rotating body 11. In an predetermined irradiation area, the emission holes 46 and a irradiation windows 43 on the irradiation processing chamber 10 and the retaining mechanism 2 for holding the container are aligned approximately on the same axes.

4 Claims, 4 Drawing Sheets

(a)

(b)

ELECTRON BEAM IRRADIATION APPARATUS FOR OPEN-MOUTHED CONTAINERS

TECHNICAL FIELD

The present invention relates to an electron beam irradiation apparatus for open-mouthed containers particularly to such an electron beam irradiation apparatus for open-mouthed containers as is capable of disinfecting insides and outsides of open-mouthed containers to a good disinfection quality with improved efficiency in irradiation of electron beam.

BACKGROUND ART

Open-mouthed containers of plastic are widely used for packing beverage, food, medical supplies, and even cosmetics. The open-mouthed containers undergo the sterilization of their insides for germfree state before filling such items to be packed; thereafter they are filled with contents and then sealed. As an alternative to the sterilization of an open-mouthed container by chemical treatment, which requires a large-scaled facility, it has been used to sterilize the inside and the outside of such container by electron beam irradiation while transferring the container at a high-speed.

Explanations are provided hereunder referring to electron beam irradiation apparatuses that sterilize the insides and the outsides of open-mouthed plastic containers typically such as PET bottles.

For example, an electron beam irradiation device has been proposed in JP 10-268100A1 (Patent Literature 1). In that device, the inside and the outside of an open-mouthed container are sterilized with electron beam while the open-mouthed container is transferred through the irradiation area that has an electron beam generating means. While in movement, the open-mouthed container is turned from upright position to laid-flat position on its side and passes through the irradiation area rolling.

As another idea, a container sterilizer by means of electron beam has been proposed in JP11-1212A1 (Patent Literature 2). In that sterilizer, an electron beam generating means is arranged vertical-longitudinally in an electron beam irradiation area. An open-mouthed container is transferred into the irradiation area in upright position to be irradiated with electron beam generated from the electron beam generating means, in which the open-mouthed container is rotated so that the inside and the outside of the open-mouthed container will be sterilized while in movement.

Similarly, a sterilization method and apparatus of vessel has been proposed in JP2002-104334A1 (Patent Literature 3). In that method, an open-mouthed container is transferred into an irradiation area in upright position to be sterilized. The irradiation area is provided with one electron beam irradiation means, which emits electron beam. The electron beam emitted from the electron beam irradiation means is deflected by alternating-current magnetic field to scan in the direction of container transfer and is shared by radially arranged nozzles so that plural containers will be sterilized one by one with irradiation while traveling.

In the electron beam irradiation device described in Patent Literature 1 cited above, the open-mouthed container is transferred in upright position, but is temporary laid flat on its side while traveling through the irradiation treatment area. Therefore integrating this device into a production line requires the device to have a laying and raising mechanism. The mechanism, when integrated however, largely lowers the line speed for transferring the open-mouthed container. Thus, the integrating of the device is a hard problem for such a production line as is required to have high production efficiency in conveying open-mouthed containers.

In contrast, the electron beam irradiation apparatus described in Patent Literature 2 can be integrated into various production lines. In tinsidehis application however, the production line should run at a reduced conveying speed or should use a high-energy electron beam generating means to sterilize fully both the inside and the outside of the open-mouthed container. This is because of the fact that, in this container sterilizer, each of the open-mouthed containers on being carried is irradiated sideways for sterilization by a single electron beam irradiation window provided on the electron beam generating means in the apparatus as it passes the irradiation window.

Further, in the electron beam irradiation apparatus described in Patent Literature 3, the single electron beam generating means should have a number of nozzles arranged radially to share emitted electron beam to irradiate each of open-mouthed containers on being conveyed in series on a production line. This requirement results in a sophisticated apparatus structure. To sterilize fully both the inside and the outside of the open-mouthed container using the apparatus described in Patent Literature 3, the production line should run at a reduced conveying speed with a problem in the enhancement of the efficiency of the production line.

To improve these situations, the inventor of the present invention proposes an electron beam irradiation apparatus for open-mouthed containers having a configuration, in which a rotating body is provided rotatively in an irradiation processing chamber, plural retaining mechanisms are installed on the outside face of the rotating body at a regular interval, open-mouthed containers are held severally on the retaining mechanism, and thereby the open-mouthed containers are rotatively conveyed in a chain at a high-speed. In this apparatus, a predetermined area in the conveying path formed between the irradiation processing chamber and the rotating body is used as an irradiation area. Above the irradiation area, an electron beam generating means is arranged to emit electron beam, which irradiates the open-mouthed containers to sterilize.

In that electron beam irradiation apparatus for open-mouthed containers, the open-mouthed containers rotatively conveyed into the irradiation area in the irradiation processing chamber are sterilized by irradiation of electron beam passed through a small irradiation window provided on the top face of the irradiation processing chamber. Therefore, the exposure dose over the open-mouthed containers decreases if the emission holes of the grid plate of the electron beam source in the electron beam generating means and the irradiation window of the irradiation processing chamber, further and, the open-mouthed container are not inline, even very slight extent. In an extreme case, the irradiation efficiency of the open-mouthed container possibly drops below half.

In the electron beam irradiation apparatuses of this kind for open-mouthed containers, electron beam is emitted continuously from electron beam generating means. Therefore, if alignment deviates from the correct positioning as stated above, the irradiation hits not only the open-mouthed containers facing the irradiation window but possibly hits also the outsides of open-mouthed containers adjacent to the target containers causing an over-dose of electron beam irradiation of the adjacent containers.

To prevent undesired irradiation of the open-mouthed containers other than intended irradiation target, it is necessary to provide some contrivance such as widening the interval of the retaining mechanisms on the rotating body and providing an electron beam shield on each of the retaining mechanisms to limit the electron beam exposure area.

These contrivances however increase dimensions of the rotating body and the irradiation processing chamber; and further, it makes the capacity of the power supply unit of the electron beam generating means large. Therefore, an electron beam irradiation apparatus intended for incorporating in a production line that conveys open-mouthed containers at a high-speed has encountered a problem of growth in overall size that prevents economical manufacture of the apparatus.

An object of the present invention is to provide such an electron beam irradiation apparatus for open-mouthed containers as offers greatly improved electron beam irradiation efficiency with efficient sterilization of open-mouthed containers and economized manufacturing by virtue of its downsized feature.

DISCLOSURE OF INVENTION

An electron beam irradiation apparatus for open-mouthed containers by the present invention having: an irradiation processing chamber; a rotating body provided rotatively in the irradiation processing chamber, a plurality of retaining mechanisms installed on the outer face of the rotating body at a regular interval, an irradiation area being a predetermined area in conveying path formed between the irradiation processing chamber and the rotating body; and an electron beam generating means arranged above the irradiation area, in which open-mouthed containers are rotatively conveyed being held by the retaining mechanisms, and insides and outsides of open-mouthed containers are sterilized in the irradiation area by irradiation of electron beam, the electron beam being emitted from the electron beam generating means and passed through irradiation windows of the irradiation processing chamber, in which the rotating body has a rotary shaft that penetrates airtightly into the electron beam generating means, the rotary shaft has a grid plate of an electron beam source of the electron beam generating means rotatively installed thereon, the grid plate has a plurality of emission holes at an interval equal to the interval of the retaining mechanisms installed on the rotating body, and the emission holes and the irradiation windows of the irradiation processing chamber and the retaining mechanisms that holds the open-mouthed container are aligned approximately on the same axes in the irradiation area.

An electron beam irradiation apparatus for open-mouthed containers by the present invention having: an irradiation processing chamber; a rotating body provided rotatively in the irradiation processing chamber, a plurality of retaining mechanisms installed on the outer face of the rotating body at a regular interval, an irradiation area being a predetermined area in conveying path formed between the irradiation processing chamber and the rotating body; and an electron beam generating means arranged above the irradiation area, in which open-mouthed containers are rotatively conveyed being held by the retaining mechanisms, and insides and outsides of open-mouthed containers are sterilized in the irradiation area by irradiation of electron beam, the electron beam being emitted from the electron beam generating means and passed through irradiation windows of the irradiation processing chamber, in which the irradiation processing chamber has a pressure reduction means to keep internal pressure of the irradiation processing chamber negative, the rotating body has a rotary shaft that penetrates airtightly into the electron beam generating means, the rotary shaft has a grid plate of an electron beam source of the electron beam generating means rotatively installed thereon, the grid plate has a plurality of emission holes at an interval equal to the interval of the retaining mechanisms installed on the rotating body, and the emission holes and the irradiation windows of the irradiation processing chamber and the retaining mechanisms that holds the open-mouthed container are aligned approximately on the same axes in the irradiation area.

It is a preferable feature in the invented apparatus that the emission holes of the grid plate for emitting electron beam and the irradiation windows of the irradiation processing chamber has apertures provided separately for irradiations inside or outside of the open-mouthed container.

It is also another preferable feature in the invented apparatus that the emission holes of the grid plate has a hole for irradiation inside an open-mouthed container and a hole for irradiation outside the open-mouthed container, and the hole for irradiation outside the open-mouthed container are arranged in a concentric circle with the hole for irradiation of the inside an open-mouthed container; the irradiation windows of the irradiation processing chamber include an inside irradiation arc gap and outside irradiation arc gaps, the inside irradiation arc gap is for irradiation inside an open-mouthed container and the outside irradiation arc gaps are for irradiation outside the open-mouthed container, the outside irradiation arc gaps are arranged on the inner side and the outer side of the inside irradiation arc gap.

EFFECT OF INVENTION

Composing an electron beam irradiation apparatus for open-mouthed containers as defined in the present invention can greatly improve irradiation efficiency in sterilization of open-mouthed containers with electron beam in the irradiation treatment area of the irradiation processing chamber because the emitted electron beam can be effectively used for irradiation inside and the outside of the open-mouthed containers without wastage. Thus, the invented apparatus is able to sterilize open-mouthed containers efficiently because electron beam irradiates the inside and the outside thereof productively without dose difference between the inside and the outside.

Irradiation efficiency thus improved permits capacity reduction of the power supply unit for the electron beam generation means. Further, the improvement enables to make the installation interval of retaining mechanisms on the rotating body narrow and to omit or to simplify the shielding and the cooling means. This feature reduces dimensions of the rotating body and the irradiation processing chamber connecting to economical manufacture of a small-sized electron beam irradiation apparatus for open-mouthed containers.

BEST MODE FOR CARRYING OUT THE INVENTION

The following explains an embodiment of the present invention referring to drawings.

Figure 1:
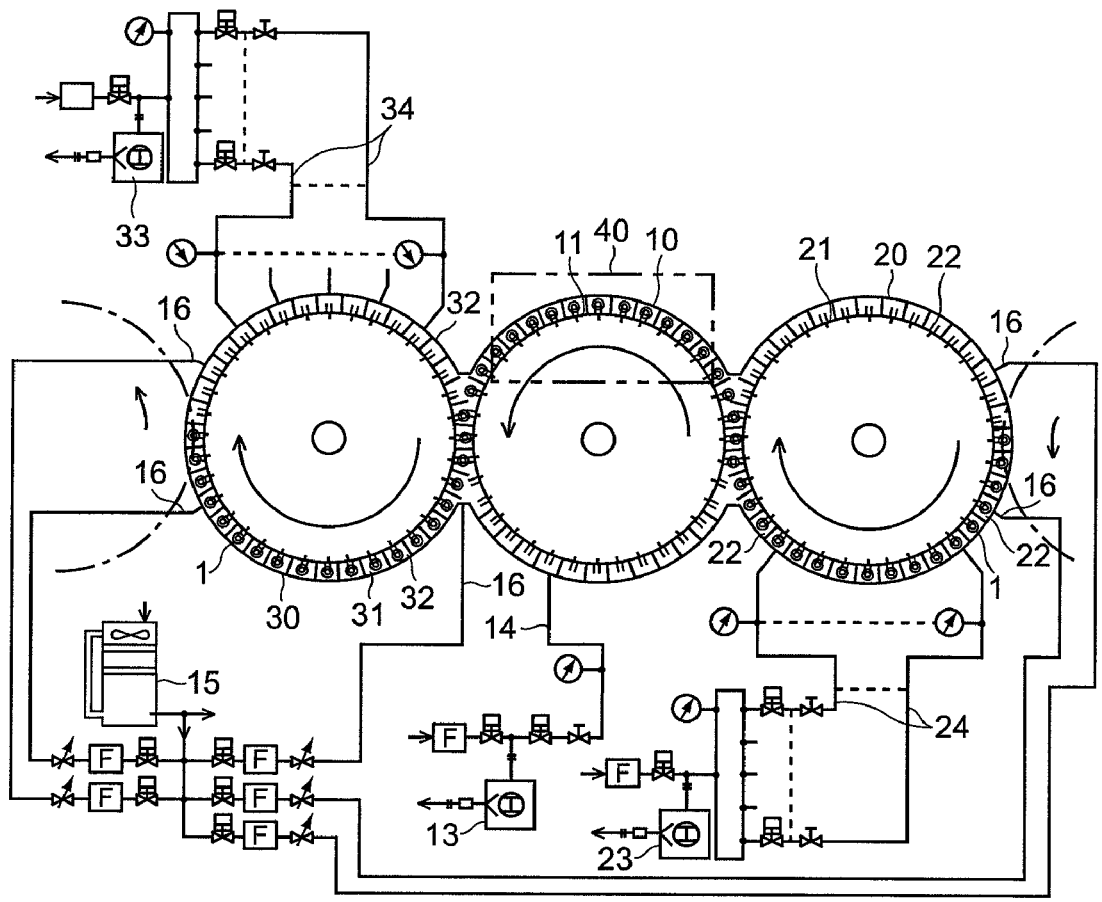
FIG. 1 is a schematic drawing of the principle of an electron beam irradiation apparatus for open-mouthed containers to which the present invention applies.
Figure 1:
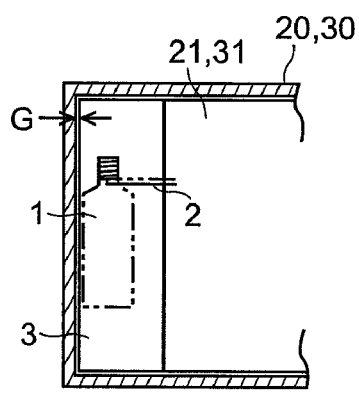

FIGS. 1(a) and 1(b) illustrate the principle of an electron beam irradiation apparatus for open-mouthed containers to which the present invention applies, in which plastic bottles are used as the open-mouthed containers. A pre-pressure adjusting bath 20 and a post-pressure adjusting bath 30 are arranged adjacent to the side face of an irradiation processing chamber 10 located between the baths 20 and 30, which are severally jointed integrally to the irradiation processing chamber 10. In the baths 10, 20, and 30, rotating bodies 11, 21, and 31 are rotatively arranged; the rotating bodies 11, 21, and 31, are rotated synchronously in the arrow-indicated directions by a driving mechanism (not illustrated).

The rotating bodies 11, 21, and 31 thus arranged form circular conveying paths, along which an open-mouthed container 1 is consecutively transferred, between the walls of baths 10, 20, and 30. Thus, the processing line for the open-mouthed container 1 has the pre-pressure adjusting bath 20, next the irradiation processing chamber 10, and lastly the post-pressure adjusting bath 30 in this order of location, in which the pre-pressure adjusting bath 20 connects with a pre-treatment line and the post-pressure adjusting bath 30 connects with a post-treatment line.

Each of the rotating bodies 11, 21, and 31 has a plurality of retaining mechanisms 2 on its outer face at a regular interval to retain the open-mouthed container 1. This retaining mechanism 2 has such a structure as enables smooth and consecutive handing-over of and receiving the open-mouthed container 1 with the open-mouthed container's position kept upright among the rotating bodies 21, 11, and 31 respectively arranged in the baths 20, 10, and 30 being located in the area from the pre-treatment line down to the post-treatment line.

In this example, the irradiation processing chamber 10 has a pressure tight sealed structure to endure the reduced pressure. A piping 14, which connects to a discharging means including an evacuation apparatus 13, is connected to the irradiation processing chamber 10; thereby the atmosphere around the open-mouthed container 1 on being transferred is maintained at a negative pressure of a predetermined level. Further, at least one electron beam generating means 40, which is connected to a power supply, is provided in such a location as faces the area in the conveying path that works as the irradiation area within the irradiation processing chamber 10. Using the electron beam generating means 40, electron beam is emitted toward the portion of the conveying path, which works as the irradiation area, in the irradiation processing chamber 10 maintained in a negative pressure to irradiate the open-mouthed container 1 being consecutively transferred for sterilization.

When sterilizing the inside and the outside of the open-mouthed container 1 in the negative-pressured irradiation processing chamber 10 with electron beam irradiation, such a device as works with lower energy of an acceleration voltages of 150 kV or lower is applicable to the electron beam generating means 40. When the irradiation processing chamber 10 is in a pressure-reduced state, attenuation of the movement of beam is largely reduced. This means as follows: the electron range (range of flight) will be extended even if the energy of the electron is low, the divergence of the beam will be small, and therefore an effective irradiation of the inside and the outside of the open-mouthed container 1 is attainable.

To enable the irradiation processing chamber 10 to maintain its negative pressure state facilitating a satisfactory irradiation of electron beam, the present invention applies a particular arrangement to the pre-pressure adjusting bath 20, which connects with the pre-treatment line as the sending-in side of the open-mouthed container 1, and to the post-pressure adjusting bath 30, which connects with the post-treatment line as the sending-out side of the open-mouthed container 1, regarding the rotating bodies 21 and 31 arranged therein. The rotating bodies 21 and 31 are made have protrusions of partitions 3, each of which sections the adjacent retaining mechanisms 2 each from the other permitting to form a plurality of small compartments 22 and 32 between both sides of the partitions 3 of the retaining mechanism 2 and the inside walls of the baths while the rotating bodies 21 and 31 rotate.

In the pre-pressure adjusting bath 20, to reduce the pressure in the small compartments 22 existing in the area between points, one at which the container 1 is conveyed in from the preceding process line and the other at which the container 1 is transferred to the irradiation processing chamber 10, a plurality of piping 24 are connected on the bath wall of such area, in which the piping 24 is connected to a discharging means including an evacuation apparatus 23. Thereby, small compartments 22 in the area between points, one at which the open-mouthed container 1 is conveyed in from the preceding process line to the pre-pressure adjusting bath 20 and the other at which the open-mouthed container 1 is transferred to the irradiation processing chamber 10, are controlled within a specified pressure range from atmospheric pressure down to a desired negative pressure.

In the post-pressure adjusting bath 30, to reduce the pressure in the small compartments 23 formed in the area between the irradiation processing chamber 10 and the point, at which the open-mouthed container 1 is conveyed out to the post-treatment line, a plurality of piping 34 are connected on the bath wall of such area, in which the piping 34 is connected to a discharging means including an evacuation apparatus 33. Thereby, small compartments 32 in the area between the irradiation processing chamber 10 and the point, at which the open-mouthed container 1 is conveyed out to the post-treatment line, are controlled within a specified range from a desired negative pressure to atmospheric pressure.

Each of the partitions 3 for forming the small compartments 22 and 32 is arranged to leave a small interstice G with the outer walls of the baths 20 and 30 as FIG. 1(b) illustrates. This construction means that one or more number of the partition 3 exist in the areas: an area between the irradiation processing chamber 10 and the open-to-atmosphere side of the pre-pressure adjusting bath 20, and an area between the bath 10 and the open-to-atmosphere side of the post-pressure adjusting bath 30. Because of these arrangements, the plural partitions 3 work like a labyrinth seal increasing the flow resistance through the irradiation processing chamber 10 to outside under atmospheric pressure. This increased flow resistance allows the irradiation processing chamber 10 to maintain its negative pressure state without particular sealing mechanism.

In the electron beam irradiation apparatus for open-mouthed containers stated above, the open-mouthed container 1 conveyed out from the preceding process line in upright position and sent-in the pre-pressure adjusting bath 20 travels from, and via this order, the pre-pressure adjusting bath 20, the irradiation processing chamber 10, and the post-pressure adjusting bath 30, and then is sent-out therefrom to the successive process line. A predetermined area in the irradiation bath 10 defined where the open-mouthed container 1 is under transfer is used as the irradiation area, in which the electron beam generating means 40 is arranged. Thus, the electron beam emitted from the electron beam generating means 40 irradiates the moving and rotating open-mouthed container 1 in the negative pressure atmosphere for sterilization thereof. Therefore, the open-mouthed container 1, which is being conveyed at a high-speed in upright position in a production line for such as beverages, can be efficiently sterilized using the electron beam generating means 40 with low energy.

Figure 2:
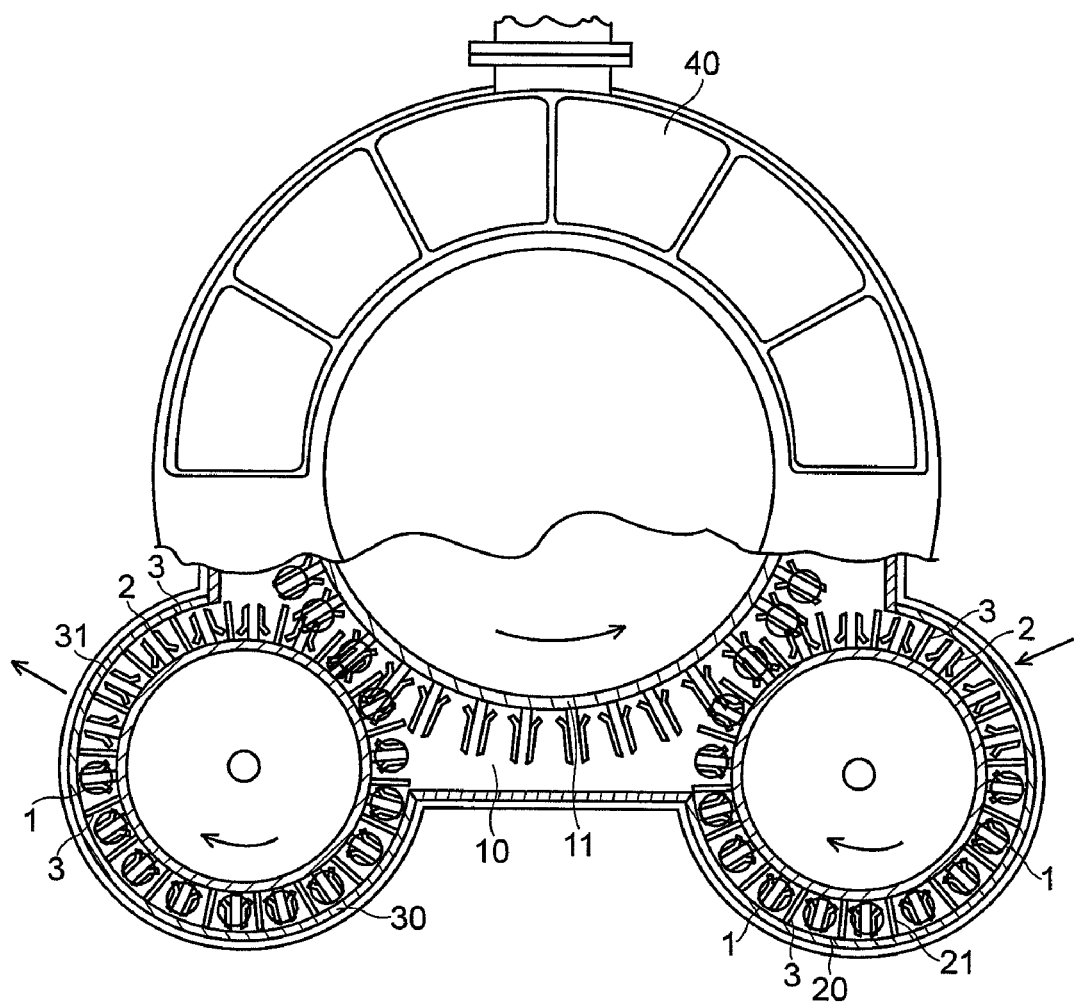
FIG. 2 is a schematic plan view of an electron beam irradiation apparatus for open-mouthed containers to illustrate a sectional aspect of a part thereof to which the present invention applies.

In the electron beam irradiation apparatus for open-mouthed containers as an embodiment of the present invention illustrated in FIG. 2, the diameter of the irradiation processing chamber 10 is designed larger than that of the pre-pressure adjusting bath 20 and the post-pressure adjusting bath 30 to each of which the irradiation processing chamber 10 is to be integrally jointed. The irradiation processing chamber 10 has at least one electron beam generating means 40 in an arc-sectoral area of the top surface thereof that faces the irradiation area in the conveying path of the open-mouthed container 1. The electron beam generating means 40 is connected to a power supply unit (not illustrated). In this configuration, the open-mouthed container 1 is sterilized by electron beam irradiation in the irradiation area of the irradiation processing chamber 10 while moving from the preceding process line to the successive process line as well as the aspects stated above.

Figure 3:
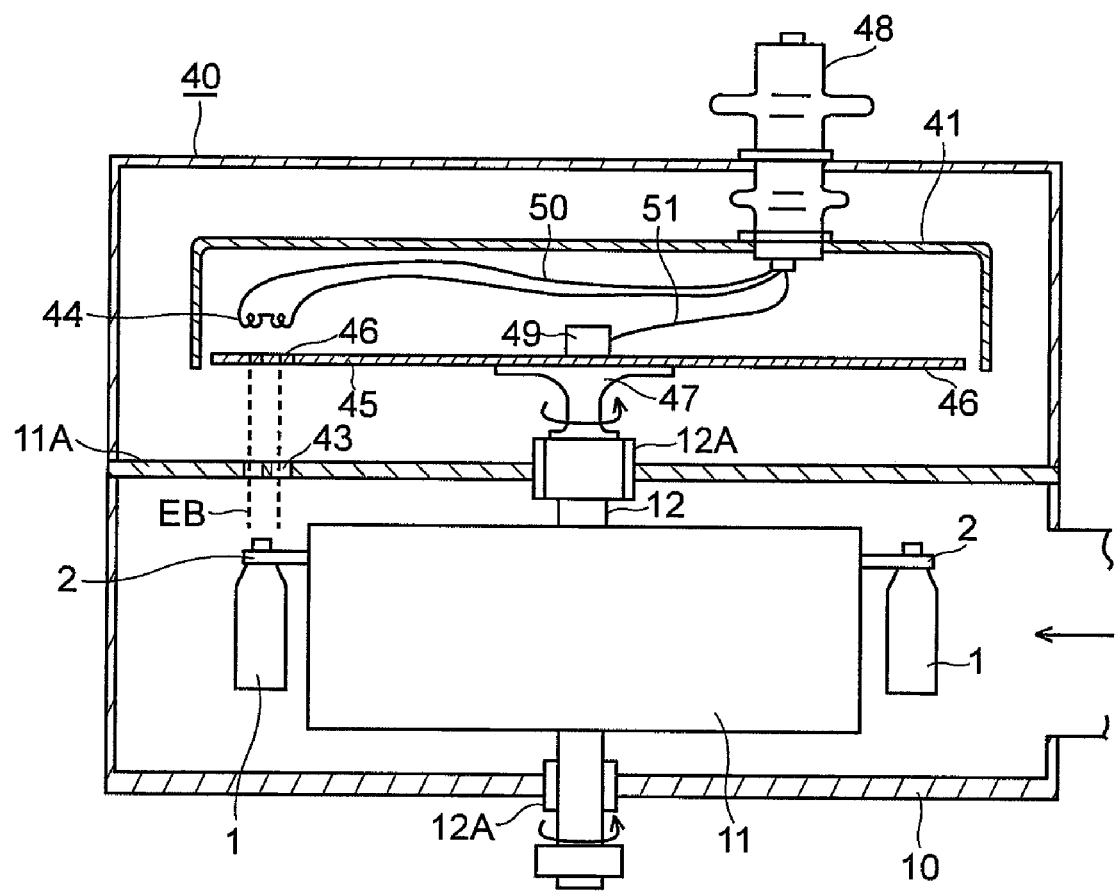
FIG. 3 is a schematic vertical sectional view of an electron beam irradiation apparatus for open-mouthed containers as an embodiment of the present invention.

FIG. 3 illustrates a limited part of the irradiation processing chamber 10 to which the present invention is applied. The irradiation processing chamber 10 has the electron beam generating means 40 on the top thereof that faces the irradiation area in the conveying path. Inside the electron beam generating means 40, an electron beam source 41 is installed. The inside of the electron beam source 41 is highly evacuated to a level such as $10^{-5}$ Pa. Electron beam EB emitted from the electron beam source 41 penetrates, as indicated with dotted lines, an irradiation windows 43 of a thin film (not illustrated) formed on a top plate 10A located above the irradiation area to irradiate the inside and the outside of the open-mouthed container 1 for sterilization.

A rotary shaft 12 of the rotating body 11 penetrates the top plate 10A of the irradiation processing chamber 10 and a part of the rotary shaft 12 protrudes inside the electron beam generating means 40. The rotary shaft 12 has a rotary vacuum seal 12A, which has a labyrinth structure capable of maintaining airtightness, on such a portion thereof as penetrates the irradiation processing chamber 10.

As commonly known, the electron beam source 41 has a filament 44 and a grid plate 45. These are connected to a power supply unit (not illustrated) through lead wires 50 and 51, and an insulated terminal that penetrates the electron beam generating means 40. With this arrangement, electron beam generated within a high vacuum is accelerated and emitted through an emission holes 46 provided on the grid plate 45 to irradiate the conveying path in the irradiation area of the irradiation processing chamber 10.

The grid plate 45 of the electron beam source 41 is rotatively secured on the rotary shaft 12, which protrudes into the electron beam generating means 40 to the present invention, using an insulative rotary supporter 47, and the rotary shaft 12 and the grid plate 45 rotate in the same direction. On the grid plate 45, which rotates, a rotary joint 49 is provided for power feeding for grid voltage. To the rotary joint 49, the lead wire 51 is connected to establish voltage feeding to the grid plate 45.

On the grid plate 45, a plurality of the emission holes 46 are arranged in a concentric circle with a position that faces the irradiation windows 43. Each of the emission holes 46 is positioned at an interval (pitch) equal to the positioning interval (pitch) of the retaining mechanisms 2 installed on the rotating body 11. With this configuration, the emission holes 46 on the grid plate 45, which rotates integrally with the rotary shaft 12, and the retaining mechanism 2, which holds the open-mouthed container 1, on the rotating body 11 turn keeping their relative position unchanged. Thus, the emission holes 46 and the open-mouthed container 1 in move being held on the retaining mechanism 2 sit vertically in almost on the same position.

Figure 4:
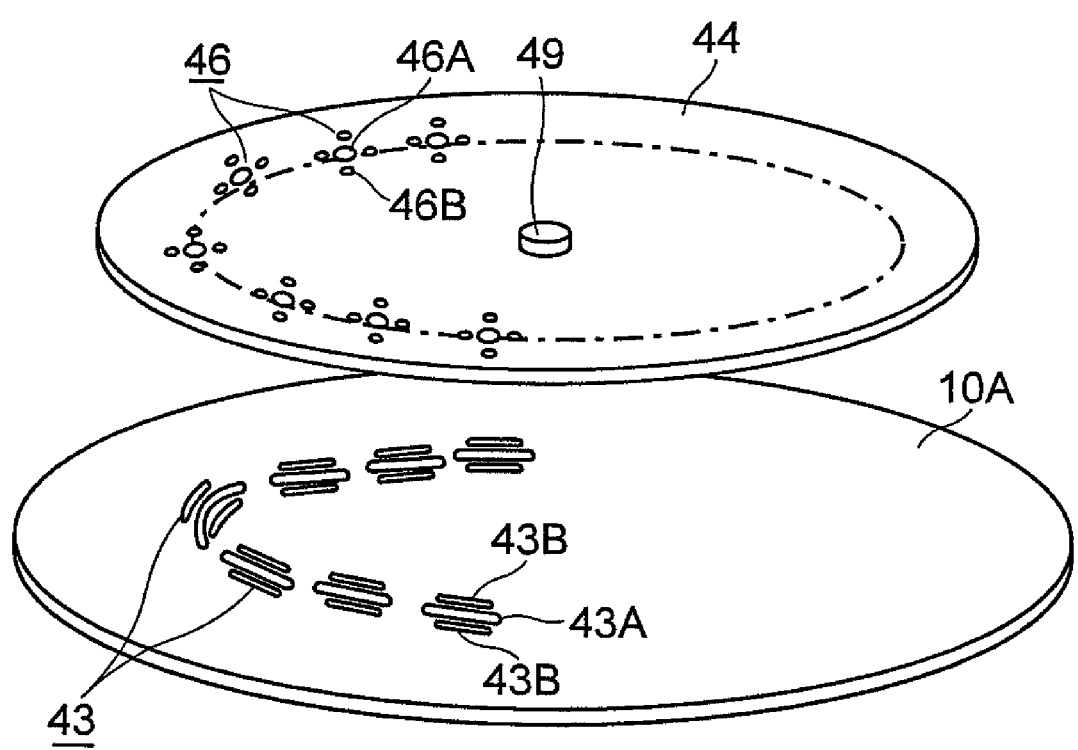
FIG. 4 is a perspective view of a typical major portion in the electron beam irradiation apparatus for open-mouthed containers illustrated in FIG. 3.

In making each of the emission holes 46 on the entire periphery of the grid plate 45 at the interval same as that of the retaining mechanisms 2, an inside irradiation hole 46A, which is to be center matched with the open-mouthed container 1, and an outside irradiation hole 46B, which is for irradiation outside of the open-mouthed container 1, are separately provided as illustrated in FIG. 4 for example. In this arrangement, the inside irradiation hole 46A in the middle, which is to introduce electron beam inside the open-mouthed container 1, is formed in a dimension larger than the outside irradiation holes 46B.

The irradiation windows 43 is provided in a plurality on the top plate 10A of the irradiation processing chamber 10 correspondingly facing the emission holes 46 on the grid plate 45 for the extent of the irradiation area. Each of the irradiation windows 43 is configured distinguishing, as illustrated in FIG. 4 for example, an inside irradiation arc gap 43A, which is given a similar size to the inside irradiation hole 46A and the outside irradiation hole 46B, and outside irradiation arc gaps 43B, which are provided on the inner and the outer side of the inside irradiation arc gap 43A. Therefore, electron beam irradiation works while the open-mouthed container 1 exists on the conveying path underneath the inside irradiation arc gap 43A and the outside irradiation arc gaps 43B.

With this configuration, the emission holes 46 on the grid plate 45 and the retaining mechanism 2 holding the open-mouthed container 1 move rotationally to reach the irradiation area of the irradiation processing chamber 10; and, while the emission holes 46 and the irradiation windows 43 and the open-mouthed container 1 are approximately in alignment on the same axes in such movement, electron beam emitted regularly from the electron beam source 41 in the electron beam generating means 40 is radiated toward the open-mouthed container 1 to apply electron beam sterilization to the inside and the outside of the open-mouthed container 1.

Therefore, the electron beam from the electron beam source 41 in the electron beam generating means 40 little produces dose difference between the inside and the outside of the open-mouthed container 1 with irradiation efficiency of electron beam greatly improved. The emission holes 46 and the retaining mechanism 2 rotationally move with their position mutually matched on the same installation intervals. This means that the electron beam irradiation to the open-mouthed container 1 will take place only while the irradiation windows 43 and the open-mouthed container 1 are approximately in alignment on the same axes. Thus, no electron beam irradiation will occur on those open-mouthed containers adjacent to the open-mouthed container 1 as the irradiation target. With this feature, the emitted electron beam can be effectively used for irradiation without wastage connecting to a great reduction in the requirement for the capacity of the power supply unit of the electron beam generating means 40.

The electron beam irradiation takes place only when the emission holes 46 and the irradiation windows 43 and the retaining mechanism 2 are approximately in alignment on the same axes; therefore, only the targeted open-mouthed containers are sterilized. This feature enables the installation interval of retaining mechanisms on the rotating body to be narrow and omission of or simplification of the shielding and the cooling means that the retaining mechanism 2 usually requires. Consequently, dimensions of not only the rotating body 11 but also the irradiation processing chamber 10 can be reduced permitting downsizing the entirety of the electron beam irradiation apparatus for open-mouthed containers with manufacturing thereof made economical.

In the above descriptions, the electron beam irradiation apparatus for open-mouthed containers as an embodiment was explained assuming that the inside of the irradiation processing chamber 10 was maintained negative pressure. The present invention however is not limited to such configuration. In the irradiation area of above-stated irradiation processing chamber 10, the configuration such that the emission holes 46 on the rotating grid plate and the irradiation windows 43 of the irradiation processing chamber 10 and the open-mouthed container 1 held on the retaining mechanism 2 are approximately in alignment on the same axes can be applicable to all the embodiment schemes, in which the inside of the irradiation processing chamber 10 is kept such as atmospheric pressure and gaseous atmosphere.

INDUSTRIAL APPLICABILITY

An electron beam irradiation apparatus for open-mouthed containers by the present invention sterilizes the inside and the outside of an open-mouthed container in an irradiation area with electron beam from an electron beam generating means. The rotary shaft of a rotating body rotatively arranged in an irradiation processing chamber of the invented apparatus penetrates airtightly into an electron beam generating means. On this rotary shaft, a grid plate of an electron beam source of the electron beam generating means is rotatively installed. The grid plate has a plurality of emission holes formed thereon at the same interval as the installation interval of retaining mechanisms of the rotating body. The emission holes and the irradiation windows of the irradiation processing chamber and the retaining mechanism to hold the open-mouthed container are arranged so that they will align approximately on the same axes in the irradiation area. With this configuration, the electron beam emitted from the electron beam generating means can be effectively used for irradiation inside and the outside of the open-mouthed containers without wastage. Thus, electron beam irradiation efficiency can be greatly improved and the open-mouthed container can be efficiently sterilized. Therefore, the present invention is suitable for the downsizing of the entirety of the electron beam irradiation apparatus for open-mouthed containers to manufacture the one economically.

The invention claimed is:

1. An electron beam irradiation apparatus for open-mouthed containers comprising:
   an irradiation processing chamber;
   a rotating body provided rotatively in the irradiation processing chamber;
   a plurality of retaining mechanisms installed on the outer face of the rotating body at a regular interval;
   an irradiation area being a predetermined area in a conveying path formed between the irradiation processing chamber and the rotating body; and
   an electron beam generating means arranged above the irradiation area, in which open-mouthed containers are rotatively conveyed being held by the retaining mechanisms, and insides and outsides of the open-mouthed containers are sterilized in the irradiation area by irradiation of electron beam, the electron beam being emitted from the electron beam generating means and passed through irradiation windows of the irradiation processing chamber,
   wherein the rotating body has a rotary shaft that penetrates airtightly into the electron beam generating means,
   the rotary shaft has a grid plate of an electron beam source of the electron beam generating means rotatively installed thereon,
   the grid plate has a plurality of emission holes at an interval equal to the interval of the retaining mechanisms installed on the rotating body, and
   the emission holes and the irradiation windows of the irradiation processing chamber and the retaining mechanisms that hold open-mouthed containers are aligned approximately on the same axes in the irradiation area.

2. The electron beam irradiation apparatus for open-mouthed containers according to claim 1,
   wherein the emission holes of the grid plate for emitting electron beam and the irradiation windows of the irradiation processing chamber comprise apertures provided separately for irradiation inside and outside an open-mouthed container.

3. The electron beam irradiation apparatus for open-mouthed containers according to claim 1,
   wherein the emission holes of the grid plate comprises a hole for irradiation inside an open-mouthed container and holes for irradiation outside the open-mouthed container, the holes for irradiation outside the open-mouthed container are arranged in a concentric with the hole for irradiation inside an open-mouthed container, and
   the irradiation windows of the irradiation processing chamber comprise an inside irradiation arc gap and outside irradiation arc gaps, the inside irradiation arc gap is for irradiation inside an open-mouthed container and the outside irradiation arc gaps are for irradiation outside the open-mouthed container, the outside irradiation arc gaps are arranged on the inner side and the outer side of the inside irradiation arc gap.

4. An electron beam irradiation apparatus for open-mouthed containers comprising:
   an irradiation processing chamber;
   a rotating body provided rotatively in the irradiation processing chamber;
   a plurality of retaining mechanisms installed on the outer face of the rotating body at a regular interval;
   an electron beam generating means arranged above the irradiation area, in which open-mouthed containers are rotatively conveyed being held by the retaining mechanisms, and insides and outsides of the open-mouthed containers are sterilized in the irradiation area by irradiation of electron beam, the electron beam being emitted from the electron beam generating means and passed through irradiation windows on the irradiation processing chamber,
   wherein the irradiation processing chamber has a pressure reduction means to keep internal pressure of the irradiation processing chamber negative,
   the rotating body has a rotary shaft that penetrates airtightly into the electron beam generating means,
   the rotary shaft has a grid plate of an electron beam source of the electron beam generating means rotatively installed thereon,
   the grid plate has a plurality of emission holes at an interval equal to the interval of the retaining mechanisms installed on the rotating body, and
   the emission holes and the irradiation windows of the irradiation processing chamber and the retaining mechanisms that hold open-mouthed containers are aligned approximately on the same axes in the irradiation area.

* * * * *